United States Patent [19]

Oku

[11] Patent Number: 5,215,077
[45] Date of Patent: Jun. 1, 1993

[54] DIRECT VISION/SIDE VISION EXCHANGEABLE ENDOSCOPE

[75] Inventor: Toshio Oku, Tokyo, Japan

[73] Assignee: Machida Endoscope Co., Ltd., Tokyo, Japan

[21] Appl. No.: 609,930

[22] Filed: Nov. 6, 1990

[30] Foreign Application Priority Data

Nov. 9, 1989 [JP] Japan .................. 1-130112[U]

[51] Int. Cl.⁵ .......................... A61B 1/00; A61B 1/06
[52] U.S. Cl. ........................................ 128/4; 128/6
[58] Field of Search ............... 128/4, 6; 403/342; 285/89, 386

[56] References Cited

U.S. PATENT DOCUMENTS

| | | | |
|---|---|---|---|
| 2,091,794 | 8/1937 | Pester | 273/80 D |
| 3,390,900 | 7/1968 | McCormick et al. | 285/89 X |
| 4,116,477 | 9/1978 | Wahoski | 285/386 X |
| 4,706,653 | 11/1987 | Yamamoto | 128/4 |
| 4,742,818 | 5/1988 | Hughes et al. | 128/4 X |
| 4,919,112 | 4/1990 | Siegmund | 128/4 |

FOREIGN PATENT DOCUMENTS

| | | | |
|---|---|---|---|
| 3735771 | 5/1988 | Fed. Rep. of Germany | 128/4 |
| 259894 | 10/1926 | United Kingdom | 285/89 |
| 393419 | 6/1933 | United Kingdom | 285/386 |

*Primary Examiner*—V. Millin
*Assistant Examiner*—J. Doyle
*Attorney, Agent, or Firm*—Levisohn, Lerner & Berger

[57] ABSTRACT

A direct vision/side vision exchangeable endoscope having two stages of small-diameter and large-diameter threads differing in their diameter are formed on the distal end of the examining portion of the endoscope. A threaded portion to be engaged with the small-diameter thread is formed on the inner side of the rear end of an attachment, and flanges are formed in the vicinity of both ends of the attachment, and an anchoring ring having a thread to be engaged with the large-diameter thread, formed on the inner side of the top end thereof, and an anchoring portion for anchoring the flanges, formed on the inner side of the rear end thereof, is freely set between both the flanges of the attachment.

4 Claims, 2 Drawing Sheets

DIRECT VISION/SIDE VISION EXCHANGEABLE ENDOSCOPE

BACKGROUND OF THE INVENTION

The present invention relates to an encoscope in which a direct-vision attachment and a side-vision attachment can be exchangeably attached as the attachment on the examining or distal end of the endoscope.

An endoscope in which a direct-vision attachment and a side-vision attachment is exchangeably attached to an object lens on the distal end of the endoscope so that one endoscope can be used as both of direct-vision and side-vision endoscopes has been known. An endoscope of this type is disclosed for example, in Japanese Laid-Open Utility Model Publication No. 62-184515.

In this conventional technique, the attachment is attached and fixed to the distal end portion of the endoscope by means of a pin inserted in the distal end portion or a thread is formed on the distal end portion.

However, the conventional attachment means is insufficient in that the attachment means is loosened by vibration or heat in an object to be examined, in which the endoscope is inserted, and there is a risk of falling of the object lens.

For example, in the case where the interior of a jet engine is inspected by the endoscope, falling of the attachment in the engine results in occurrence of a grave accident. Similarly, there is a risk of falling of the attachment when the body cavity is examined by the endoscope.

It is a primary object of the present invention to provide a direct vision/side vision exchangeable endoscope in which the attachment is kept attached even if the anchoring ring comes off, and falling of the attachment is prevented.

Another object of the present invention is to provide a direct vision/side vision exchangeable endoscope in which the effect of preventing falling of the attachment is similarly attained, even if the anchoring ring is freely set on the distal end portion.

Still another object of the present invention is to provide a direct vision/side vision exchangeable endoscope in which an operator can be informed of the loosing of the anchoring ring and occurrence of an accident can be prevented, in case of the side-vision attachment.

Still a further object of the present invention is to provide a direct vision/side vision exchangeable endoscope in which the anchoring ring and the attachment are presented from simultaneously coming off under the same conditions, even if there are motions in one direction of the endoscope, and an assured securement can be expected.

SUMMARY OF THE INVENTION

In accordance with the present invention, there is provided a direct vision/side vision exchangeable endoscope, characterized in that two stages of small-diameter and large-diameter screws differing in then diameter are formed on the examining end of a distal end portion of the endoscope, a thread to be engaged with the small-diameter thread is formed on the inner side of the rear end of an attachment, flanges are formed in the vicinity of both the ends of the attachment, and an anchoring ring having a thread to be engaged with the large-diameter thread, formed on the inner side of the top end thereof, and an anchoring portion for anchoring the flanges, formed on the inner side of the rear end thereof, is freely set between both the flanges of the attachment.

Furthermore, according to the present invention, there is provided a direct vision/side vision exchangeable endoscope, characterised in that a thread is formed on the distal end of a distal end portion of the endoscope, and an anchoring ring capable of moving in the front-rear direction and turning in the axial direction is fitted through a flange, a thread is formed on the inner side of the anchoring ring, a thread to be engaged with the thread on the distal end of the distal end portion of the endoscope is formed on the inner circumference of the rear end of an attachment, and a screw to be engaged with the screw of the anchoring ring is formed on the outer circumference of the rear end of the attachment.

In the endoscope having the above-mentioned structure, the attachment is fixed to the top end hard portion of the endoscope by means of the threads, and the anchoring ring is further screwed, whereby a double-lock structure can be formed and falling of the attachment can be assuredly prevented.

DETAILED DESCRIPTION OF THE PREFERRED EMBODIMENTS

Enbodiments of the present device will now be described with reference to the accompanying drawings.

Figure 1:
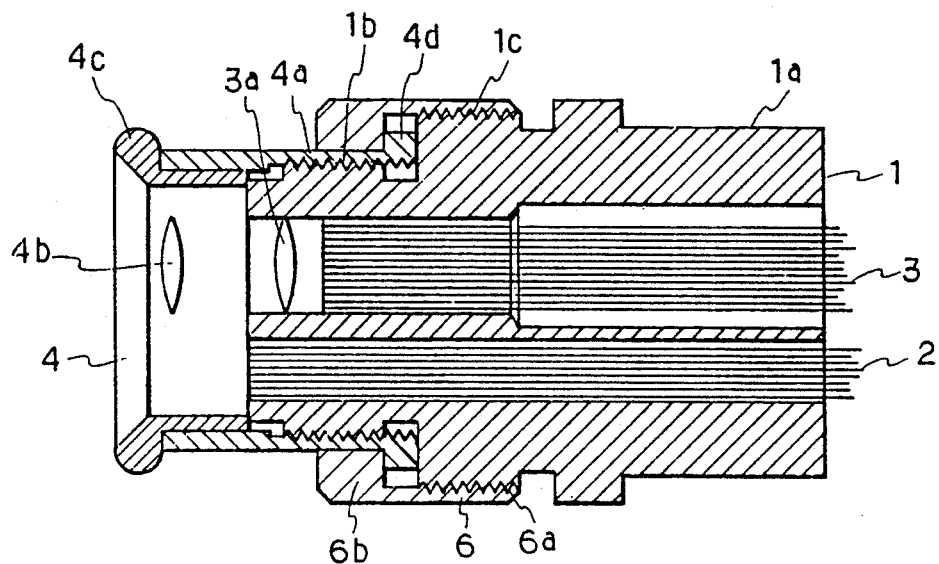
FIG. 1 is a sectional view illustrating the first embodiment in which the direct-vision attachment is fitted.
Figure 2:
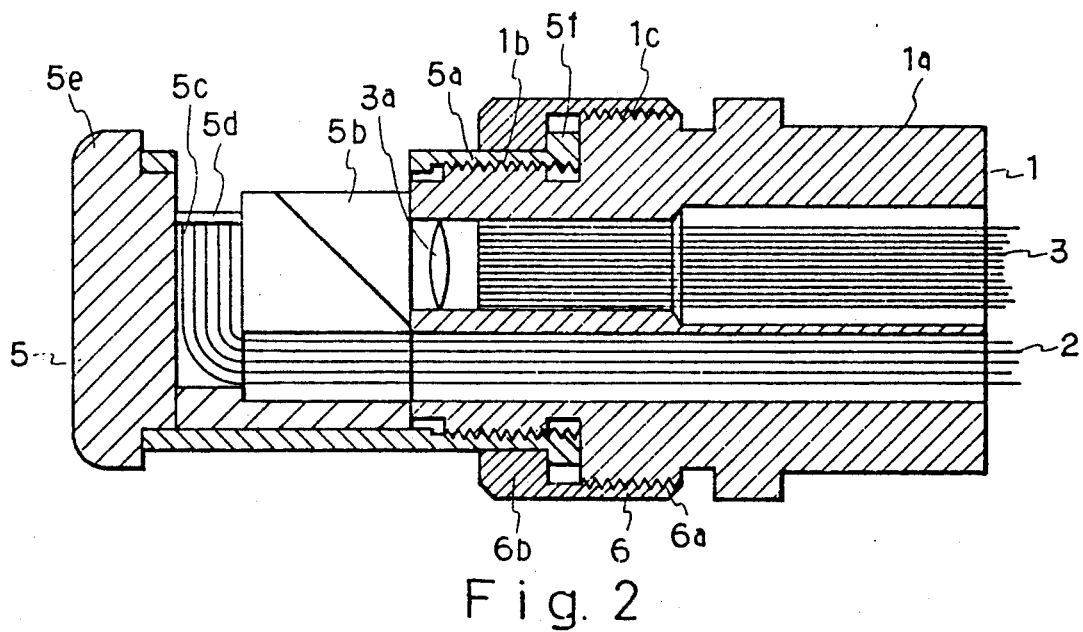
FIG. 2 is a sectional view illustrating the first embodiment in which the side-vision attachment is fitted.

FIG. 1 is a sectional view illustrating a first embodiment in which the direct-vision attachment is fitted, and FIG. 2 is a sectional view illustrating the first embodiment in which the side-vision attachment is fitted.

In the drawings, reference numeral 1 represents a distal end portion of the endoscope, and at least a light guide 2 and an image guide 3 are passed through the distal end portion 1, and a lens system 3a is arranged on the distal end of the image guide 3. If necessary, an air or water conduit and a forceps-introducing tube are passed through the distal end hard portion 1, and a step 1a is formed at the rear part of the outer circumference of the distal end hard portion 1. This top end hard portion 1 is connected to a flexible tube, not shown in the drawings, of the endoscope, and an endo portion of an outer casing covering the flexible tube also covers this step 1a.

Reference numeral 1b represents a first threaded section and reference numeral 1c represents a second threaded section, and the threads of section 1b and 1c are reverse to each other. The diameter of the second screw 1c is larger than the diameter of the first section 1b.

Reference numeral 4 represents a direct-vision attachment, and a screw 4a to be engaged with the first screw 16 is formed on the inner side of the rear end of the attachment 4. According to need, an object lens 4b is also arranged on the attachment 4. Reference numerals 4c and 4d represent flanges formed on the outer circumference at both the ends of the attachment 4.

Reference numeral 5 represents a side-vision attachment, and a threaded portion 5a to be engaged with the first threaded portion 1*b* is formed on the inner side of the rear end of the attachment 5 and a viewing window is formed on the side face of the attachment 5. A light-refracting means compraising a mirror, a prism and the like 5*b* is arranged to be frontal this side face. A glass or lens window 5*d* is formed on the distal end face of a light guide 5*c*. Reference numerals 5*e* and 5*f* represent flanges formed on the outer circumference at both ends of the attachment 5.

Reference numeral 6 represents an anchoring ring, and a threaded protion 6*a* to be engaged with the second threaded portion 1*c* is formed on the inner side of the distal end and the anchoring ring 6 is fitted between both the flanges of the attachment so that the ring 6 can move in the front-rear direction and can turn relative to the axis. An anchoring portion 6*b* is formed on the inner side of the rear end of the ring 6.

According to the embodiment having the above-mentioned structure, the direct vision or side-vision attachment is selected and attached to the top end hard portion 1. Since the function is almost the same irrespective of the kind of the selected attachment, the function will now be described with reference to the side-vision attachment 5.

At first, the threaded portion 5*a* of the side-vision attachment 5 is screwed and attached to the first threaded portion 1*b* of the distal end portion 1 so that the refracting means 5*b* is in front of the image guide 3 of the top end hard portion 1 and the light guide 5*c* is in front of the light guide 2.

Then, the threaded portion 6*a* of the anchoring ring 6 fitted in the side-vision attachment 4 is engaged with the second threaded portion 1*c* of the distal end hard portion 1, whereby the bear against and anchoring portion 6*b* anchors the flange 5*f* and the attachment 5 is further fastened.

Thus, the threaded portion 5*a* of the attachment 5 is engaged with the first threaded portion 1*b* of the distal end hard portion 1 and the attachment 5 is integrated with the distal end hard portion 1, and when the anchoring ring 6 is fitted and screwed in place, the integration degree is enhanced. At this point, the directions of the screw 5*a* of the attachment 5 and the threads 6*a* of the anchoring ring 6 are opposite to each other.

When the attachment thus attached is dismounted, the anchoring ring 6 is first dismounted and the attachment 5 is rotated.

Since the direct-vision attachment 4 is attached and dismounted substantially in the same manner as described above with respect to the attachment 5, the explanation is omitted.

In the above-mentioned first embodiment, the directions of the first and second threads 1*b* and 1*c* respectively are opposite to each other. In a second embodiment not shown in the drawings, the direction is the same in both for the first and second threaded sections but the threads have different pitches and corresponding threaded sections are formed on the respective attachments and the anchoring ring. Also in this embodiment, there can be attained effects similar to those attained in the first embodiment.

Figure 3:
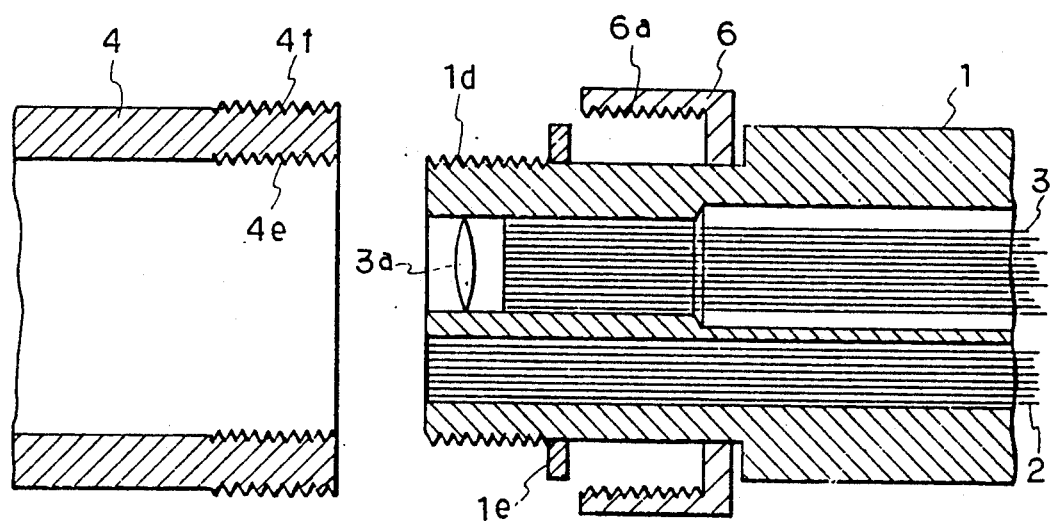
FIG. 3 is a sectional view illustrating a main part of the third embodiment.

FIG. 3 is a sectional view showing a main part of a third embodiment. A threaded section 1*d* is formed on the distal end of a distal end portion 1, and then, through a flange 1*e*, an anchoring ring 6 is fitted, as in the first embodiment, so that the anchoring ring 6 can move in the front-rear direction and can turn in the axial direction. A threaded section 6*a* is formed on the inner side of the anchoring ring 6, and the direction of this thread 6*a* is opposite to the direction of the threaded section 1*d* or both the threads are in the screw direction but with different pitches.

Since direct-vision and side-vision attachments are similar to each other, only the direct-vision attachments will now be described.

A threaded section 4*e* to be engaged with the screw 1*d* is formed on the inner circumference of the rear end of the direct-vision attachment 4, and a threaded section 4*f* to be engaged with the threaded section 6*a* is formed on the outer circumference thereof.

In the above-mentioned structure, the threaded section 4*e* of the direct-vision attachment 4 is screwed onto and fixed to the threaded portion 1*d* of the distal end hard portion 1, and then, the anchoring ring 6 is attached to the threaded sections 4*f* of the attachment 4, whereby the attachment 4 is fixed and integrated with the distal end hard portion 1.

In the above-mentioned structure of the third embodiment, the arrangements of the distal end of the distal end portion 1 and the attachment 4 can be reversed. Also in this case, the above effects are similarly attained.

As is apparent from the foregoing description, according to the present device, the directions of small-diameter and large-diameter screws are opposite to each other or are cut in the same direction at different pitches. If this structure is adopted, when the attachment is attached to the distal end hard portion of the endoscope, the attachment is directly screwed to the distal end hard portion and is anchored by the anchoring ring. Therefore, even if the anchoring ring comes off, the attachment is still attached and falling of the attachment is prevented.

Furthermore, even if the anchoring ring is freely set on the distal end hard portion, the effect of preventing falling of the attachment is similarly attained by the double-lock structure.

Moreover, in case of the side-vision attachment, if the anchoring ring comes off, the visual field is disturbed by the anchoring ring, an operator can be informed of the coming-off of the anchoring ring and occurrence of an accident can be prevented.

Still further, since the small-diameter and large-diameter threads are opposite to each other or are cut in the same direction at different pitches, even if there is motions in one direction of the endoscope, the anchoring ring and the attachment are caused to simultaneously come off under the same conditions, and therefore, an assured fixation state can be expected.

What is claimed is:

1. A direct vision exchangeable endoscope having a detachable attachment member attached to the distal end, said endoscope has first and second threaded portions of differing diameters at the distal end portion of said endoscope, said attachment member having a threaded section adapted to engage with the smaller one of said first or second threaded sections of said endoscope, said attachment member comprising first and second retention flanges located at opposite ends of said attachment member, an anchoring ring having an anchoring portion thereof located between said flanges, said anchoring ring having a threaded portion to engage the other of said first or second threaded portion of said endoscope, said anchoring portion capturing one of said retention flanges between the anchoring ring and the distal end of the said endoscope, the threads of said first and second threaded portions being different to require different forces to separate the respectively joined members at said first and second threaded portions, the direction of threads of said first and second threaded sections being opposite to each other whereby the detachable attachment can only be removed by separating the joined members at the respective first and second threaded portions such that accidentally dropping of the attachment from the endoscope is prevented.

2. The invention is set forth in claim 1, wherein said first threaded portion has a smaller diameter than said second threaded portion.

3. A side vision exchangeable endoscope having a detachable attachment member attached to the distal end, said endoscope has first and second threaded portions of differing diameters at the distal end portion of said endoscope, said attachment member having a threaded section adapted to engage with the smaller one of said first or second threaded sections of said endoscope, said attachment member comprising first and second retention flanges located at opposite ends of said attachment member, an anchoring ring having an anchoring portion thereof located between said flanges, said anchoring ring having a threaded portion to engage the other of said first or second threaded portion of said endoscope, said anchoring portion capturing one of said retention flanges between the anchoring ring and the distal end of said endoscope, the threads of said first and second threaded portions being different to require different forces to separate the respectively joined members at said first and second threaded portions, the direction of threads of said first and second threaded sections being opposite to each other whereby the detachable attachment can only be removed by separating the joined members at the respective first and second threaded portions such that accidentally dropping of the attachment from the endoscope is prevented.

4. The invention is set forth in claim 3, wherein said first threaded portion has a smaller diameter than said second threaded portion.

* * * * *